US008591875B2

(12) United States Patent
Belcheva et al.

(10) Patent No.: US 8,591,875 B2
(45) Date of Patent: *Nov. 26, 2013

(54) BIODEGRADABLE PHOSPHOESTER POLYAMINES

(75) Inventors: Nadya Belcheva, Hamden, CT (US); Ahmad R. Hadba, Wallingford, CT (US)

(73) Assignee: Covidien LP, Mansfield, MA (US)

(*) Notice: Subject to any disclaimer, the term of this patent is extended or adjusted under 35 U.S.C. 154(b) by 1418 days.

This patent is subject to a terminal disclaimer.

(21) Appl. No.: 12/160,929

(22) PCT Filed: Feb. 22, 2007

(86) PCT No.: PCT/US2007/004477
§ 371 (c)(1),
(2), (4) Date: Jul. 15, 2008

(87) PCT Pub. No.: WO2007/100574
PCT Pub. Date: Sep. 7, 2007

(65) Prior Publication Data
US 2008/0279807 A1      Nov. 13, 2008

Related U.S. Application Data

(60) Provisional application No. 60/775,749, filed on Feb. 22, 2006.

(51) Int. Cl.
*A61K 31/80* (2006.01)
*C08G 79/04* (2006.01)
(52) U.S. Cl.
USPC ........ 424/78.02; 424/423; 424/426; 525/418; 525/538; 525/438
(58) Field of Classification Search
USPC ............ 424/78.02, 426, 78.27, 423; 528/398, 528/271, 55, 73, 10; 525/418, 538, 403, 525/404, 438, 453
See application file for complete search history.

(56) References Cited

U.S. PATENT DOCUMENTS

| 3,668,154 | A | | 6/1972 | Buisson |
| 4,425,472 | A | | 1/1984 | Howard et al. |
| 5,256,765 | A | * | 10/1993 | Leong ........................ 528/398 |
| 5,578,662 | A | | 11/1996 | Bennett et al. |
| 5,717,030 | A | | 2/1998 | Dunn et al. |
| 5,990,237 | A | | 11/1999 | Bentley et al. |
| 6,071,530 | A | | 6/2000 | Polson et al. |
| 6,261,544 | B1 | | 7/2001 | Coury et al. |
| 6,395,823 | B1 | | 5/2002 | Brink et al. |
| 6,495,127 | B1 | | 12/2002 | Wallace et al. |
| 6,582,713 | B2 | | 6/2003 | Newell et al. |
| 7,129,300 | B2 | * | 10/2006 | Roby ........................ 525/408 |
| 2003/0032734 | A1 | | 2/2003 | Roby |
| 2003/0135238 | A1 | | 7/2003 | Milbocker |
| 2004/0068078 | A1 | | 4/2004 | Milbocker |
| 2004/0198901 | A1 | | 10/2004 | Graham et al. |
| 2005/0004661 | A1 | | 1/2005 | Lewis et al. |
| 2005/0069573 | A1 | | 3/2005 | Cohn et al. |
| 2005/0147647 | A1 | | 7/2005 | Glauser et al. |

FOREIGN PATENT DOCUMENTS

| EP | 0 913 416 A1 | 5/1999 |
| FR | 2 487 819 | 2/1982 |
| WO | WO 03/011173 A2 | 2/2003 |

OTHER PUBLICATIONS

International Search Report from Application No. EP 07 75 1249 mailed May 25, 2010 (5 pages).
Dewa, Takehisa, et al., "Novel Polyamine-Dialkyl Phosphate Conjugates for Gene Carriers. Facile Synthetic Route via an Unprecedented Dialkyl Phosphate", *Bioconjugate Chem.*, vol. 15, pp. 824-830 (2004).
Geall, Andrew J., et al., "Efficient Calf Thymus DNA Condensation Upon Binding with Novel Bile Acid Polyamine Amides", *Bioconjugate Chem.*, vol. 13, pp. 481-490 (2002).

* cited by examiner

*Primary Examiner* — James J Seidleck
*Assistant Examiner* — S. Camilla Pourbohloul

(57) ABSTRACT

Novel biodegradable phosphoester polyamines are disclosed. The biodegradable phosphoester polyamines may be utilized as cross-linkers for sprayable compositions which may be used as tissue adhesives or sealants.

11 Claims, No Drawings

BIODEGRADABLE PHOSPHOESTER POLYAMINES

CROSS-REFERENCE TO RELATED APPLICATIONS

This application is a National State Application of PCT/US2007/004477 under 35USC §371 (a), which claims priority of U.S. Provisional Patent Application Ser. No. 60/775,749 filed Feb. 22, 2006, the disclosures of each of the above-identified applications are hereby incorporated by reference in their entirety.

BACKGROUND

1. Technical Field

The present disclosure relates to biodegradable phosphoester polyamines and their use in the formation of compositions, such as adhesives or tissue sealants.

2. Background of Related Art

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

For surgical adhesives to be accepted by surgeons, they should exhibit high initial tack and an ability to bond rapidly to living tissue; the strength of the bond should be sufficiently high to cause tissue failure before bond failure; the adhesive should form a bridge, typically a permeable flexible bridge; and the adhesive bridge and/or its metabolic products should not cause local histotoxic or carcinogenic effects.

Several materials useful as tissue adhesives or tissue sealants are currently available. One type of adhesive that is currently available is a cyanoacrylate adhesive. However, cyanoacrylate adhesives can have a high flexural modulus which can limit their usefulness. Another type of tissue sealant that is currently available utilizes components derived from bovine and/or human sources. For example, fibrin sealants are available. However, as with any natural material, variability in the material can be observed. It would be desirable to provide a fully synthetic biological adhesive or sealant.

SUMMARY

The present disclosure provides biodegradable phosphoester polyamines. The biodegradable phosphoester polyamines include, in embodiments, polyamine functionalized phosphoester-ester-ether oligomers and polymers. These biocompatible compositions may be utilized as cross-linkers for sprayable compositions. The sprayable compositions include, in embodiments, tissue adhesives and sealants, including multiisocyanate-polyether-polyurethane sealants.

In embodiments, the present disclosure provides a biocompatible composition including a biodegradable phosphoester polyamine of the following formula:

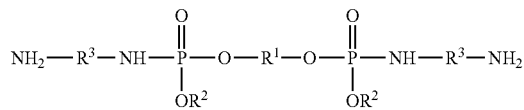

wherein $R^1$ is selected from the group consisting of polyethers, polyesters, poly(ether-ester) blocks and combinations thereof, $R^2$ is a hydrogen atom, a protecting group or an organic moiety having from about 1 to about 50 carbon atoms, and $NH-R^3-NH_2$ is derived from a polyamine selected from the group consisting of ethylene diamine, hexamethylene diamine, lysine, N-(3-aminopropyl)-1,4-butanediamine, N,N'-bis(3-aminopropyl)-1,4-butanediamine, isomers of hexamethylene diamine, diethylene triamine, triethylene tetramine, tetraethylene pentamine, bishexamethylene triamine, N,N'-bis(3-aminopropyl)-1,2-ethane diamine, N-(3-Aminopropyl)-1,3-propane diamine, N-(2-aminoethyl)-1,3 propane diamine, cyclohexane diamine, isomers of cyclohexane diamine, 4,4'-methylene biscyclohexane amine, 4'4'-methylene bis(2-methylcyclohexanamine), toluene diamine, phenylene diamine, isophorone diamine, phenalkylene polyamines, amino-functionalized polyalkylene oxides, polypeptides, and combinations thereof.

In other embodiments, the present disclosure provides compositions including an isocyanate prepolymer and a biodegradable phosphoester polyamine of the following formula:

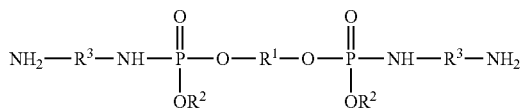

wherein $R^1$ is selected from the group consisting of polyethers, polyesters, poly(ether-ester) blocks and combinations thereof, $R^2$ is a hydrogen atom, a protecting group or an organic moiety having from about 1 to about 50 carbon atoms, and $NH-R^3-NH_2$ is derived from a polyamine selected from the group consisting of ethylene diamine, hexamethylene diamine, lysine, N-(3-aminopropyl)-1,4-butanediamine, N,N'-bis(3-aminopropyl)-1,4-butanediamine, isomers of hexamethylene diamine, diethylene triamine, triethylene tetramine, tetraethylene pentamine, bishexamethylene triamine, N,N'-bis(3-aminopropyl)-1,2-ethane diamine, N-(3-Aminopropyl)-1,3-propane diamine, N-(2-aminoethyl)-1,3 propane diamine, cyclohexane diamine, isomers of cyclohexane diamine, 4,4'-methylene biscyclohexane amine, 4'4'-methylene bis(2-methylcyclohexanamine), toluene diamine, phenylene diamine, isophorone diamine, phenalkylene polyamines, amino-functionalized polyalkylene oxides, polypeptides, and combinations thereof, wherein the biodegradable phosphoester polyamine crosslinks the isocyanate prepolymer.

In other embodiments, the present disclosure provides processes including combining a hydroxyl-terminated component with a phosphoester to form a phosphoester functionalized compound, and combining the phosphoester functionalized compound with a polyamine to produce a biodegradable phosphoester polyamine.

DETAILED DESCRIPTION

The present disclosure relates to novel biodegradable phosphoester polyamines. The phosphoester polyamines are biocompatible, non-immunogenic and biodegradable. In embodiments, the biodegradable phosphoester polyamines may be utilized as cross-linkers for tissue adhesives and sealants, including multiisocyanate-polyether-polyurethane sealants. Such sealants may be employed to adhere tissue edges, seal air/fluid leaks in tissues, adhere medical devices, i.e.

implants, to tissue, and for tissue augmentation such as sealing or filling voids or defects in tissue. The compositions can be applied to living tissue and/or flesh of animals, including humans.

The biodegradable phosphoester polyamines of the present disclosure may include polyamine functionalized phosphoester-ester-ether oligomers and polymers. In embodiments, the biodegradable phosphoester polyamine may be generated by endcapping a hydroxyl-terminated component with a phosphoester, optionally in the presence of an amine such as a tertiary amine. The phosphoester group may then be endcapped with a polyamine having at least one primary/secondary amino group. Methods for reacting polyamines with phosphoester groups are within the purview of those skilled in the art and include, for example, the methods disclosed in Dewa et al., "Novel Polyamine-Dialkyl Phosphate Conjugates for Gene Carriers. Facile Synthetic Route via an Unprecedented Dialkyl Phosphate." Bioconjugate Chem. 2004, 15, pp. 824-830, the entire disclosure of which is incorporated by reference herein.

Suitable hydroxyl-terminated components include, for example, hydroxyl-terminated polyethers, polyesters, and/or poly(ether-ester) blocks. Suitable polyethers which may be utilized are within the purview of those skilled in the art and include, for example, polymers and copolymers of polyethylene glycol, polypropylene glycol, polybutylene glycol, polytetramethylene glycol, polyhexamethylene glycol, and combinations thereof. Suitable polyesters which may be utilized are within the purview of those skilled in the art and include, for example, polymers and copolymers of trimethylene carbonate, ε-caprolactone, p-dioxanone, glycolide, lactide, 1,5-dioxepan-2-one, polybutylene adipate, polyethylene adipate, polyethylene terephthalate, and combinations thereof. Suitable poly(ether-ester) blocks are within the purview of one skilled in the art and include, but are not limited to, polyethylene glycol-polycaprolactone, polyethylene glycol-polylactide, polyethylene glycol-polyglycolide and various combinations of the individual polyethers and polyesters described herein. Additional examples of poly(ether-ester) blocks are disclosed in U.S. Pat. No. 5,578,662 and U.S. Patent Application No. 2003/0135238, the entire contents of each of which are incorporated by reference herein.

In embodiments, the hydroxyl-terminated precursor components can be polyethylene glycol, methoxy polyethylene glycol, glycolide-polyethylene glycol-caprolactone copolymers, aliphatic oligoesters, combinations thereof, and the like.

Suitable phosphoesters which may be utilized to endcap the hydroxyl-terminated precursor components include, but are not limited to, dichloro-phosphoesters such as ethyl dichlorophosphate (EOP). In embodiments, the hydroxyl-terminated precursor may be combined with the phosphoester in an organic solvent such as tetrahydrofuran (THF), dimethylformamide (DMF), dichloromethane ($CH_2Cl_2$), combinations thereof, and the like. In other embodiments, the phosphoester may be combined with the hydroxyl-terminated precursor in the presence of an amine such as a tertiary amine. Suitable tertiary amines which may be utilized include, for example, triethylamine, dimethylaminopropylamine, pyridine, dimethylaniline, N,N-dimethylaniline, N-ethylpiperidine, N-methylpyrrolidine, N,N,N',N'-tetramethylethylenediamine, N,N,N',N'-tetramethylethylenediamine, 1,2-dipiperidinoethane, trimethylaminoethylpiperazine, N,N,N',N'',N''-pentamethylethylenetriamine, N,N'-dioctyl-p-phenylenediamine, combinations thereof, and the like.

In embodiments, the reaction scheme for functionalizing the hydroxyl-terminated precursor component with a phosphoester may include the following:

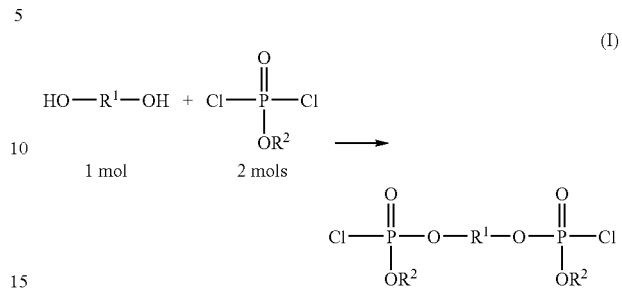

wherein $R^1$ may be a polyether, polyester, and/or poly(ether-ester) block as described above, or combinations thereof, and $R^2$ may be a hydrogen atom, a protecting group or an organic moiety containing from about 1 to about 50 carbon atoms, in embodiments from about 2 to about 20 carbon atoms.

The phosphoester functionalized compound thus produced may then be endcapped with a polyamine having at least one primary or secondary amino group. Suitable polyamines having at least one primary/secondary amino group include, but are not limited to, ethylene diamine, hexamethylene diamine, lysine, spermidine (N-(3-aminopropyl)-1,4-butanediamine), spermine (N,N-bis(3-aminopropyl)-1,4-butanediamine), isomers of hexamethylene diamine, diethylene triamine, triethylene tetramine, tetraethylene pentamine, bishexamethylene triamine, N,N-bis(3-aminopropyl)-1,2-ethane diamine, N-(3-Aminopropyl)-1,3-propane diamine, N-(2-aminoethyl)-1,3 propane diamine, cyclohexane diamine, isomers of cyclohexane diamine, 4,4'-methylene biscyclohexane amine, 4'4'-methylene bis(2-methylcyclohexanamine), toluene diamine, phenylene diamine, isophorone diamine, and phenalkylene polyamines. In embodiments, combinations of the foregoing polyamines may be utilized.

In another embodiment, the polyamine may be a polyamino functional macromer compound, including polyoxyalkylene amines sold under the name JEFFAMINE® by Huntsman Performance Chemicals (Houston, Tex.), other amino-functionalized polyalkylene oxides, polypeptides including polypeptides having lysine and/or arginine residues, and the like. In some embodiments, combinations of any of the foregoing polyamines may be utilized.

In embodiments, the phosphoester functionalized compound may be endcapped with the polyamine in accordance with the following reaction scheme.

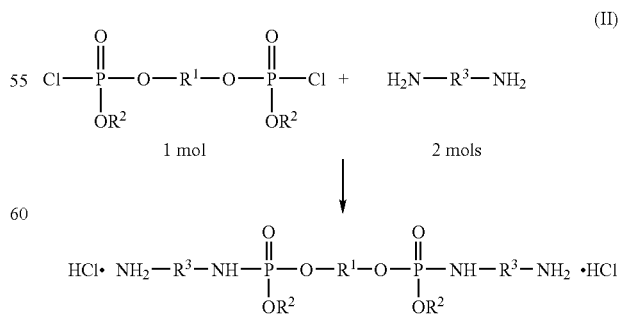

wherein $R^1$ and $R^2$ may be as defined above and NH—$R^3$—$NH_2$ may be derived from the polyamine described above.

The resulting biodegradable phosphoester polyamines of the present disclosure may be utilized in numerous medical applications. In embodiments, the biodegradable phosphoester polyamines of the present disclosure may be used as a crosslinker for a tissue adhesive or sealant. For example, the biodegradable phosphoester polyamine of the present disclosure may be utilized as a cross-linker for a sprayable multi-isocyanate-polyurethane sealant. In such an embodiment, the biodegradable phosphoester polyamines of the present disclosure may be combined with a second component such as an isocyanate prepolymer represented by the formula:

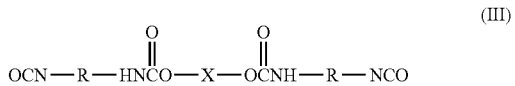
(III)

wherein X is a polyether, a polyester or a polyether-ester group; and R is an aromatic, aliphatic, or alicyclic group.

Suitable polyethers which may be utilized as a component of the isocyanate prepolymer are within the purview of those skilled in the art and include, for example, polyethylene glycol, polypropylene glycol, polybutylene glycol, polytetramethylene glycol, polyhexamethylene glycol. In a particularly useful embodiment the polyether is polyethylene glycol or a derivative thereof, such as methoxy polyethylene glycol.

Suitable polyesters which may be utilized as a component of the isocyanate prepolymer are within the purview of those skilled in the art and include, for example, trimethylene carbonate, s-caprolactone, p-dioxanone, glycolide, lactide, 1,5-dioxepan-2-one, polybutylene adipate, polyethylene adipate, and polyethylene terephthalate.

In addition, the second component may include a poly(ether-ester) block. Any suitable poly(ether-ester) block within the purview of those skilled in the art may be utilized as a component of the isocyanate prepolymer. Some examples include, but are not limited to, polyethylene glycol-polycaprolactone, polyethylene glycol-polylactide, polyethylene glycol-polyglycolide and various combinations of the individual polyethers and polyesters described herein. Additional examples of poly(ether-ester) blocks are disclosed in U.S. Pat. No. 5,578,662 and U.S. Patent Application No. 2003/0135238, the entire contents of each of which are incorporated by reference herein.

In addition to the polyether, polyester or poly(ether-ester) block, the second component may be endcapped with an isocyanate to produce a diisocyanate-functional compound. Suitable isocyanates for endcapping the aliphatic polyether, polyester or poly(ether-ester) block include aromatic, aliphatic and alicyclic isocyanates. Examples include, but are not limited to, aromatic diisocyanates such as 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenylisocyanate) or tetramethylxylylene diisocyanate; aliphatic diisocyanates such as tetramethylene diisocyanate, hexamethylene diisocyanate, dimethyl diisocyanate, lysine diisocyanate, 2-methylpentane-1,5-diisocyanate, 3-methylpentane-1,5-diisocyanate or 2,2,4-trimethylhexamethylene diisocyanate; and alicyclic diisocyanates such as isophorone diisocyanate, cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate or commercially available DESMODURS® from Bayer Material Science.

Methods for endcapping the polyether, polyester or poly(ether-ester) block with a diisocyanate are within the purview of those skilled in the art. In some embodiments, the polyether, polyester or poly(ether-ester) block may be combined with a suitable diisocyanate, in embodiments a toluene diisocyanate, and heated to a suitable temperature from about 55° C. to about 75° C., in embodiments from about 60° C. to about 70° C., in embodiments about 65° C. In some embodiments the resulting diisocyanate-functional compound may then be obtained by hot extraction with petroleum ether.

The viscosity of the second component may be from about 10 cP to about 500,000 cP, in embodiments from about 100 cP to about 200,000 cP, typically from about 200 cP to about 100,000 cP.

In embodiments, the second component may be mixed with a polar solvent. Suitable polar solvents which may be utilized are within the purview of those skilled in the art and include, for example, water, alcohols such as ethanol, triethylene glycol, methoxy-polyethylene glycols, dimethylformamide, dimethylacetamide, gamma-butyrolactone, N-methylpyrrolidone, ketones such as methylethyl ketone, cyclohexanone, ethers such as diethyl ether, and mixtures of these and other polar solvents.

The polar solvent may be mixed with the second component at a ratio of from about 1:0.25 to about 1:10 w/w, in embodiments at a ratio of from about 1:1 to about 1:4 w/w.

The mixture of the second component and polar solvent as described herein may result in an emulsion or a diluted solution. The viscosity of the resulting emulsion or solution may be below about 400 cP, in embodiments below about 200 cP. In some embodiments, the viscosity of the resulting emulsion or solution may be from about 5 cP to about 400 cP, in other embodiments from about 25 cP to about 300 cP, in still other embodiments from about 50 cP to about 150 cP. The decreased viscosity improves the spraying of the emulsion or solution without sacrificing the adherence and physico-mechanical properties of the composition as an adhesive, sealant or drug delivery system.

In addition to the polar solvents described herein, it is envisioned that the second component may also be mixed with polar drugs. As with the polar solvent, the polar drugs may react with the second component and produce an emulsion or solution with a reduced viscosity. The second component may be mixed with the polar drug and optionally a second component in situ to form synthetic drug delivery systems. Any suitable polar drug within the purview of those skilled in the art may be used.

The biodegradable phosphoester polyamines of the present disclosure in combination with the optional second component described above may thus be utilized, in embodiments, to produce biocompatible compositions of the present disclosure. The biocompatible compositions of the present disclosure may, in embodiments, be utilized as a tissue adhesive or sealant.

The biodegradable phosphoester polyamines of the present disclosure may be mixed with the second component in any manner within the purview of those skilled in the art. In some embodiments, as noted above, the second component may be combined with a polar solvent. In other embodiments, the biodegradable phosphoester polyamines of the present disclosure may be in an aqueous solution which, in turn, is combined with the second component optionally in combination with a polar solvent as described above.

One example includes keeping an emulsion or solution including the second component and polar solvent separate from the biodegradable phosphoester polyamines of the present disclosure and spraying the individual ingredients in a consecutive manner onto the same location, thereby allowing the two ingredients to mix and form a bond in situ. Another example includes keeping the emulsion or solution including the second component and polar solvent separate from the biodegradable phosphoester polyamines of the present disclosure and spraying the two ingredients simultaneously through the same nozzle, thereby allowing the two ingredients to mix while being sprayed.

The concentrations of the biodegradable phosphoester polyamines and the second component will vary depending upon a number of factors, including the types and molecular weights of the particular components used and the desired end use application, i.e., to form a composition of the present disclosure for use as an adhesive or sealant.

Where the biodegradable phosphoester polyamines and the second component are combined to produce adhesives or sealants, biologically active agents, sometimes referred to herein as bioactive agents, may be included in the compositions of the present disclosure. For example, naturally occurring polymers, including proteins such as collagen and derivatives of various naturally occurring polysaccharides such as glycosaminoglycans, can be incorporated into the composition of the present disclosure.

When these other biologically active agents also contain functional groups, the groups will react with the functional groups on the first and/or second components of the biocompatible composition of the present disclosure.

A variety of optional ingredients including medicinal agents may also be added to the biocompatible compositions of the present disclosure. A phospholipid surfactant that provides antibacterial stabilizing properties and helps disperse other materials in the biocompatible composition may be added. Additional medicinal agents include antimicrobial agents, colorants, preservatives, or medicinal agents such as, for example, protein and peptide preparations, antipyretic, antiphlogistic and analgesic agents, anti-inflammatory agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilator agents, antiviral agents and dysuric agents.

Imaging agents such as iodine or barium sulfate, or fluorine, can also be combined with the compositions of the present disclosure to allow visualization of the surgical area through the use of imaging equipment, including X-ray, MRI, and CAT scan.

Additionally, an enzyme may be added to the composition of the present disclosure to increase its rate of degradation. Suitable enzymes include, for example, peptide hydrolases such as elastase, cathepsin G, cathepsin E, cathepsin B, cathepsin H, cathepsin L, trypsin, pepsin, chymotrypsin, γ-glutamyltransferase (γ-GTP) and the like; sugar chain hydrolases such as phosphorylase, neuraminidase, dextranase, amylase, lysozyme, oligosaccharase and the like; oligonucleotide hydrolases such as alkaline phosphatase, endoribonuclease, endodeoxyribonuclease and the like. In some embodiments, where an enzyme is added, the enzyme may be included in a liposome or microsphere to control the rate of its release, thereby controlling the rate of degradation of the biocompatible composition of the present disclosure. Methods for incorporating enzymes into liposomes and/or microspheres are known to those skilled in the art.

The biocompatible composition of the present disclosure can be used for a number of different human and animal medical applications including, but not limited to, wound closure (including surgical incisions and other wounds), adhesives for medical devices (including implants), sealants, and embolic agents. These compositions may be used to bind tissue together either as a replacement of, or as a supplement to, sutures, staples, tapes and/or bandages. Use of the disclosed compositions as an adhesive can eliminate or substantially reduce the number of sutures normally required during current practices, and eliminate the subsequent need for removal of staples and certain types of sutures and thus can be particularly useful for use with delicate tissues where sutures, clamps or other conventional tissue closure mechanisms may cause further tissue damage.

Additional applications include sealing tissues to prevent or control blood, or other fluid leaks, at suture or staple lines. In another embodiment, the biocompatible composition can be used to attach skin grafts and position tissue flaps during reconstructive surgery. In still another embodiment, the adhesive can be used to close tissue flaps in periodontal surgery.

To effectuate the joining of two tissue edges, the two edges are approximated, and the composition of the present disclosure is applied, in embodiments, by spraying. The biodegradable phosphoester polyamines and the second component crosslink rapidly, generally taking less than one minute. The composition of the present disclosure can be used as an adhesive to close a wound, including a surgical incision. In such a case, the composition of the present disclosure can be applied to the wound and allowed to set, thereby closing the wound.

While certain distinctions may be drawn between the usage of the terms "flesh" and "tissue" within the scientific community, the terms are used interchangeably herein as referring to a general substrate upon which those skilled in the art would understand the present adhesive to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic or ascite tissue.

In another embodiment, the present disclosure is directed to a method for using the biocompatible composition of the present disclosure to adhere a medical device to tissue, rather than secure two edges of tissue. In some embodiments, depending on the composition of the medical device, a coating may be required on the medical device. In some cases such a coating can include the biodegradable phosphoester polyamines or the second component of the composition of the present disclosure. In some aspects, the medical device includes an implant. Other medical devices include, but are not limited to, pacemakers, stents, shunts and the like. Generally, for adhering a device to the surface of animal tissue, the composition of the present disclosure can be applied to the device, the tissue surface or both. The device, biocompatible composition and tissue surface are then brought into contact with each other and the composition is allowed to set, thereby adhering the device and surface to each other.

The compositions of the present disclosure can also be used to prevent post surgical adhesions. In such an application, the biocompatible composition is applied and cured as a layer on surfaces of internal tissues in order to prevent the formation of adhesions at a surgical site during the healing process.

In addition to the formation of adhesion barriers, in embodiments the biocompatible compositions may be utilized to form implants such as gaskets, buttresses, or pledgets for implantation.

When used as a sealant, the composition of the present disclosure can be used in surgery to prevent or inhibit bleeding or fluid leakage both during and after surgical procedure. It can also be applied to prevent air leaks associated with pulmonary surgery. The sealant may be applied directly to the desired area in at least an amount necessary to seal off any defect in the tissue and seal off any fluid or air movement.

The present biocompatible composition has a number of advantageous properties. The resulting biocompatible compositions of the present disclosure are safe and biocompatible, possess enhanced adherence to tissue, are biodegradable, have hemostatic potential, have low cost, and are easy to prepare and use. By incorporating phosphoester and optionally ester bonds in the biodegradable phosphoester polyamines of the present disclosure, the adhesive or sealant composition of the present disclosure prepared from the biodegradable phosphoester polyamine and second component described herein may be more susceptible to non-specific hydrolysis, faster degradation, and faster mass loss, without any negative effects to the mechanical performance of the adhesive or sealant upon initial application in situ.

The following Examples are being submitted to illustrate embodiments of the present disclosure. These Examples are intended to be illustrative only and are not intended to limit the scope of the present disclosure. Also, parts and percentages are by weight unless otherwise indicated.

Example 1

A biodegradable phosphoester polyamine was synthesized by functionalizing a methoxy polyethylene glycol with a phosphoester, and then endcapping the phosphoester with a polyamine.

A methoxy polyethylene glycol having a molecular weight of about 1900 (mPEG) was combined with ethyl dichlorophosphate (EOP) in the presence of triethylamine (NEt$_3$) and dimethylaminopyridine (DMAP) to form a phosphoester terminated methoxy polyethylene glycol. The mPEG, NEt$_3$, and DMAP were combined in a flask containing dichloromethane (250 mL). The flask was placed in an ice bath, so the reaction took place at a temperature of about 0-3° C. A solution containing EOP and dichloromethane was then added dropwise to flask for about 2.5 hours. The crude mixture was placed in a refrigerator and stored overnight for about 19 hours. The compounds utilized in the synthesis are set forth below in Table 1:

TABLE 1

| Compound | MW | Mols | Weight(g) | Mol Ratio |
| --- | --- | --- | --- | --- |
| mPEG 1900 (Alfa Aesar, Lot # B12L29 (m.p. 52)) | 1900 | 0.01 | 19 | 1 |
| Ethyl dichlorophosphate (Aldrich, Batch # 03509AC) | 163 | 0.01 | 1.63 (started with 1.732 dissolved in 10 mL CH$_2$Cl$_2$) | 1 |

TABLE 1-continued

| Compound | MW | Mols | Weight(g) | Mol Ratio |
| --- | --- | --- | --- | --- |
| DMAP (Aldrich # 359882 Lot # 14121PB) (2.67 mMol per 1 g) | 2.67 mMol per 1 g | 0.0025 | ~1 | 0.25 |
| Triethylamine (Burdick & Jackson Lot # CH130) | 101 | 0.015 | 1.515 | 1.5 |

The general reaction scheme for the synthesis of this phosphoester functionalized mPEG was as follows:

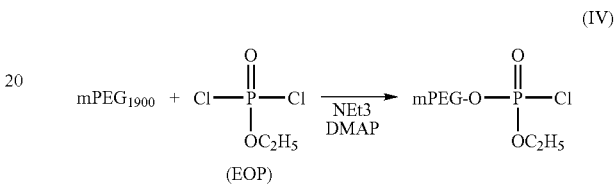

(IV)

After filtration, the resulting solution of phosphoester terminated mPEG was then reacted with spermine to form an amine terminated phosphoester functional mPEG. Spermine was dissolved in about 10 mL of dimethylformamide (DMF) and triethylamine was added to act as an HCl scavenger. The compounds utilized in this part of the synthesis and their amounts are set forth below in Table 2:

TABLE 2

| Compound | MW | Mols | Weight(g) | Mol Ratio |
| --- | --- | --- | --- | --- |
| Spermine | 202 | 0.01 | 2.02 | 1 |
| Triethylamine | 101 | 0.015 | 1.515 | 1.5 |

The spermine/trimethylamine/DMF solution was added dropwise to the phosphoester functionalized mPEG at a temperature of about 0° C. After a period of about 4 hours a precipitate was obtained. The material was subjected to filtering and evaporation: the filtrate was a colorless liquid. After reducing the volume about 90% through evaporation the resulting material was precipitated in PE/ether. After precipitation in ether, the white solid precipitate obtained was dried on a vacuum pump for about one week. Fourier transform infrared (FTIR), and nuclear magnetic resonance (NMR) analysis were used to confirm the structure of the final product. The general reaction scheme for the synthesis of this biodegradable phosphoester polyamine was as follows:

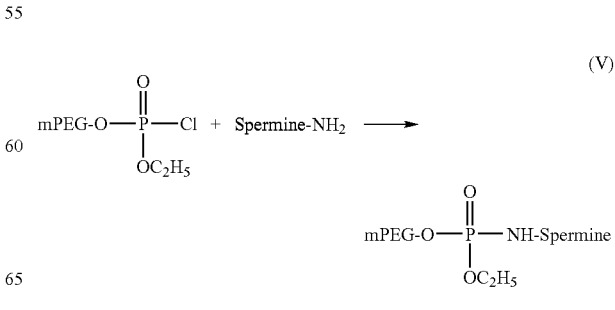

(V)

Example 2

A methoxy polyethylene glycol was functionalized with a phosphoester as generally described in Example 1 above.

Polyethylene glycol having a molecular weight of about 200 (PEG), triethylamine (NEt3) and dimethylaminopyridine (DMAP) were dissolved in dichloromethane. The materials were combined in a flask and cooled down to about 0° C. A solution containing dichloromethane and ethyl dichlorophosphate (EOP) was added dropwise under nitrogen. The reaction occurred at a temperature of about 0° C. and was allowed to proceed for about 2 hours. The materials were then stored overnight.

The compounds utilized in the synthesis are set forth below in Table 3:

TABLE 3

| Compound | MW | Mols | Weight(g) | Mol Ratio |
|---|---|---|---|---|
| PEG 200 (Aldrich, Lot # 05714JF) | 200 | 0.02 | 4 | 1 |
| Ethyl dichlorophosphate (Aldrich, Batch # 03509AC) | 163 | 0.04 | 6.52 | 2 |
| DMAP (Aldrich # 359882 Lot # 14121PB) (2.67 mMol per 1 g) | 2.67 mMol per 1 g | 0.005 | ~2 | 0.25 |
| Triethylamine (Burdick & Jackson Lot # CH130) | 101 | 0.06 | 6.06 | 3 |

The resulting material was subjected to filtering and evaporation of the filtrate on a ROTAVAPOR® rotary evaporator, (BÜCHI Labortechnik AG), then collected by precipitation in ether to obtain a dry white precipitate. The precipitate was redissolved in about 150 mL of DMF and filtered again.

Spermine was dissolved in about 150 mLs of DMF and triethylamine was added to act as a HCl scavenger. The spermine was then added to the precipitate described above. The compounds utilized in this part of the synthesis and their amounts are set forth below in Table 4:

TABLE 4

| Compound | MW | Mols | Weight(g) | Mol Ratio |
|---|---|---|---|---|
| Spermine | 202 | 0.04 | 8.08 | 2 |
| Triethylamine | 101 | 0.06 | 6.06 | 3 |

The DMF solution of spermine/trimethylamine was added dropwise to the phosphoester functionalized PEG-200 at a temperature of about 0° C. with stirring overnight. The resulting material was collected by filtering the salt of DMF under vacuum at about 60° C. The final product obtained was a viscous oil. Yield was >90% and the structure was confirmed by NMR, IR and differential scanning calorimetry (DSC).

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A biocompatible composition comprising:
a biodegradable phosphoester polyamine of the following formula:

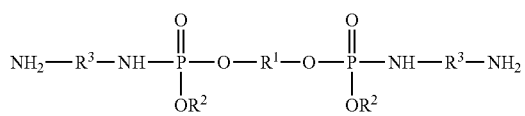

wherein $R^1$ is selected from the group consisting of polyethers, polyesters, poly(ether-ester) blocks and combinations thereof, $R^2$ is a hydrogen atom, a protecting group or an organic moiety having from about 1 to about 50 carbon atoms, and $NH-R^3-NH_2$ is derived from a polyamine selected from the group consisting of ethylene diamine, hexamethylene diamine, lysine, N-(3-aminopropyl)-1,4-butanediamine, N,N'-bis(3-aminopropyl)-1,4-butanediamine, isomers of hexamethylene diamine, diethylene triamine, triethylene tetramine, tetraethylene pentamine, bishexamethylene triamine, N,N'-bis(3-aminopropyl)-1,2-ethane diamine, N-(3-Aminopropyl)-1,3-propane diamine, N-(2-aminoethyl)-1,3 propane diamine, cyclohexane diamine, isomers of cyclohexane diamine, 4,4'-methylene biscyclohexane amine, 4'4'-methylene bis(2-methylcyclohexanamine), toluene diamine, phenylene diamine, isophorone diamine, phenalkylene polyamines, amino-functionalized polyalkylene oxides, polypeptides, and combinations thereof.

2. The biocompatible composition of claim 1, wherein $R^1$ comprises a polyether selected from the group consisting of polyethylene glycol, methoxy polyethylene glycol, polypropylene glycol, polybutylene glycol, polytetramethylene glycol, polyhexamethylene glycol, copolymers thereof, and combinations thereof.

3. The biocompatible composition of claim 1, wherein $R^1$ comprises a polyester selected from the group consisting of trimethylene carbonate, ε-caprolactone, p-dioxanone, glycolide, lactide, 1,5-dioxepan-2-one, polybutylene adipate, polyethylene adipate, polyethylene terephthalate, and combinations thereof.

4. The biocompatible composition of claim 1, wherein $R^1$ comprises a poly(ether-ester) block selected from the group consisting of polyethylene glycol-polycaprolactone, polyethylene glycol-polylactide, polyethylene glycol-polyglycolide, and combinations thereof.

5. The biocompatible composition of claim 1, wherein $R^1$ is selected from the group consisting of polyethylene glycol, methoxy polyethylene glycol, glycolide-polyethylene glycol-caprolactone copolymers, aliphatic oligoesters, and combinations thereof.

6. An adhesive comprising the biocompatible composition of claim 1.

7. A sealant comprising the biocompatible composition of claim 1.

8. A biocompatible composition comprising:
an isocyanate prepolymer; and
a biodegradable phosphoester polyamine of the following formula:

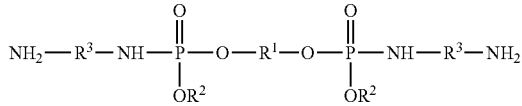

wherein $R^1$ is selected from the group consisting of polyethers, polyesters, poly(ether-ester) blocks and combinations thereof, $R^2$ is a hydrogen atom, a protecting group or an organic moiety having from about 1 to about 50 carbon atoms, and $NH-R^3-NH_2$ is derived from a polyamine selected from the group consisting of ethylene diamine, hexamethylene diamine, lysine, N-(3-aminopropyl)-1,4-butanediamine, N,N'-bis(3-aminopropyl)-1,4-butanediamine, isomers of hexamethylene diamine, diethylene triamine, triethylene tetramine, tetraethylene pentamine, bishexamethylene triamine, N,N'-bis(3-aminopropyl)-1,2-ethane diamine, N-(3-Aminopropyl)-1,3-propane diamine, N-(2-aminoethyl)-1,3 propane diamine, cyclohexane diamine, isomers of cyclohexane diamine, 4,4'-methylene biscyclohexane amine, 4'4'-methylene bis(2-methylcyclohexanamine), toluene diamine, phenylene diamine, isophorone diamine, phenalkylene polyamines, amino-functionalized polyalkylene oxides, polypeptides, and combinations thereof,
wherein the biodegradable phosphoester polyamine crosslinks the isocyanate prepolymer.

9. The biocompatible composition of claim 8, wherein the isocyanate prepolymer is of the formula

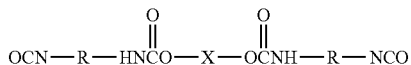

wherein X is selected from the group consisting of polyethers, polyesters and polyether-esters, and R is selected from the group consisting of aromatic groups, aliphatic groups, and alicyclic groups.

10. A method for adhering tissue comprising:
approximating a first tissue surface and a second tissue surface; and
applying the biocompatible composition of claim 8 to the approximated first and second tissue surfaces to adhere the first tissue surface to the a second tissue surface.

11. A method for adhering a medical device to a tissue surface, the method comprising:
approximating a medical device and a tissue surface; and
applying the biocompatible composition of claim 8 to the medical device, to the tissue surface, or both,
wherein applying the biocompatible composition adheres the medical device to the tissue surface.

* * * * *